United States Patent [19]
Lavielle et al.

[11] Patent Number: 5,472,979
[45] Date of Patent: Dec. 5, 1995

[54] 1,2,3,4-TETRAHYDRONAPHTHALENE COMPOUNDS

[75] Inventors: Gilbert Lavielle, La Celle Saint Cloud; Thierry Dubuffet, L'Hay les Roses; Olivier Muller, Ennery; Michel Laubie, Vaucresson; Tony Verbeuren, Vernouillet; Serge Simonet, Conflans Sainte Honorine; Jean-Jacques Descombes, Neuilly-Plaisance, all of France

[73] Assignee: Adir et Compagnie, Courbevoie, France

[21] Appl. No.: 323,508

[22] Filed: Oct. 14, 1994

[30] Foreign Application Priority Data

Oct. 15, 1993 [FR] France ...................... 93 12237

[51] Int. Cl.⁶ .................................. A61K 31/14
[52] U.S. Cl. .................. 514/562; 514/538; 514/539; 514/456; 514/357; 562/430; 560/10; 546/333; 549/404
[58] Field of Search ............ 562/430; 514/562, 514/538, 539, 456, 357; 560/10; 546/333; 549/404

[56] References Cited

U.S. PATENT DOCUMENTS 5,206,428  4/1993  Nakai et al. .................... 562/427

OTHER PUBLICATIONS

Proc. Natl. Acad. Sci. USA, 89, pp. 8155–8159 (Sep. 1992), Neurobiology section.
Annual Reports in Medicinal Chemistry, 27, pp. 21–29 entitled "Chapter 3. Advances in Central Serotoninergics" (1992).
Annual Reports in Medicinal Chemistry, 29, pp. 43–51 entitled "Chapter 5. Recent Advances in Dopamine $D_3$ and $D_4$ Receptor Ligands and Pharmacology" (1994).

Primary Examiner—José G. Dees
Assistant Examiner—Samuel Barts
Attorney, Agent, or Firm—Gordon W. Hueschen

[57] ABSTRACT

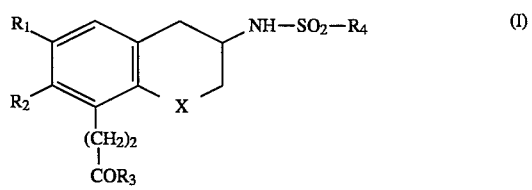

in which:

$R_1$ and $R_2$, which may be identical or different, represent hydrogen or halogen, alkyl, substituted or unsubstituted phenyl, benzyl, pyridylmethyl or imidazolylmethyl or thiazolylmethyl, pyridyl, imidazolyl or thiazolyl, or alternatively, $R_1$ and $R_2$ form, with the carbon atoms to which they are attached, cyclopentane or cyclohexane, $R_3$ represents hydroxyl, linear or branched ($C_1$–$C_6$) alkoxy or unsubstituted or substituted amino, $R_4$ represents alkyl, unsubstituted or substituted phenyl, naphthyl, pyridyl or thienyl, X represents methylene or oxygen or sulfur, its enantiomers and its addition salts with a pharmaceutically acceptable base, and medicinal products containing the same are useful as anti-thrombotic.

7 Claims, No Drawings

1,2,3,4-TETRAHYDRONAPHTHALENE COMPOUNDS

The present invention relates to a new 1,2,3,4-tetrahydronaphthalene compounds.

More particularly, the compounds described in the present invention possess anti-thromboxane $A_2$ properties which are equally good as antagonists of the thromboxane $A_2$ ($TXA_2$) receptors and as inhibitors of the activity of the enzyme responsible for the synthesis of thromboxane $A_2$: thromboxane $A_2$-synthase.

Thromboxane $A_2$ is a metabolite of arachidonic acid produced by blood platelets, which brings about a considerable constriction of blood vessels and induces aggregation of the platelets. The production of thromboxane $A_2$ is increased in conditions such as angina pectoris or strokes and it plays a very important role in all the processes leading to thrombotic conditions.

It was thus particularly advantageous to synthesize substances capable of inhibiting the pro-aggregating and vasoconstrictive activities of thromboxane $A_2$, either as thromboxane $A_2$-receptor antagonists or as thromboxane $A_2$-synthase inhibitor.

Besides the fact that they are novel, the compounds described in the present invention possess markedly more intense pharmacological properties than those of the other compounds described in the prior art.

They are thus useful as thromboxane $A_2$ antagonists and as thromboxane $A_2$-synthase inhibitors in the treatment or prevention of diseases involving thromboxane $A_2$ such as, for example, cardio- and cerebrovascular diseases and thrombotic diseases, as well as the vascular complications which accompany the pathological conditions involving either thromboxane $A_2$ or substances which interact with the $TXA_2$ receptor (for example such as the vascular complications in diabetes). These thromboxane $A_2$ antagonists also possess protective properties with respect to the gastric wall (M. L. OGLETREE et al., J. Pharm. and Exp. Therap., 263 (1), 374–380). Finally, their inhibitory properties with respect to platelet aggregation allow them to be also useful in the treatment of migraine (P . PUIG-PARELLADA et al., Prostaglandins Leukotrienes and Essential Fatty Acids, 49, 537–547, 1993).

More specifically, the present invention relates to the compounds of formula (I):

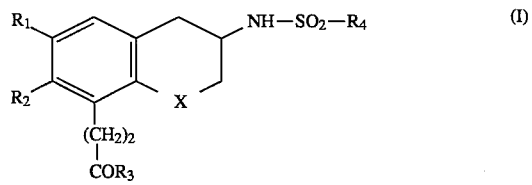

in which:

$R_1$ and $R_2$, which may be identical or different, represent a hydrogen or halogen atom, a linear or branched ($C_1$–$C_6$) alkyl group, a phenyl group (unsubstituted or substituted with one or more halogen atoms or linear or branched ($C_1$–$C_6$) alkyl groups, linear or branched ($C_1$–$C_6$) alkoxy groups, hydroxyl or trihalomethyl groups), a benzyl group, a pyridylmethyl group, an imidazolylmethyl group, a thiazolylmethyl group, a pyridyl group, an imidazolyl group or a thiazolyl group, or alternatively, $R_1$ and $R_2$ form, with the carbon atoms to which they are attached, a cyclopentane or cyclohexane ring, $R_3$ represents a hydroxyl group, a linear or branched ($C_1$–$C_6$) alkoxy group or an amino group (unsubstituted or substituted with one or two linear or branched ($C_1$–$C_6$) alkyl groups), $R_4$ represents a linear or branched ($C_1$–$C_6$) alkyl group, a phenyl group (unsubstituted or substituted with one or more halogen atoms or linear or branched ($C_1$–$C_6$) alkyl groups, linear or branched ($C_1$–$C_6$) alkoxy groups, trihalomethyl or hydroxyl groups), a naphthyl group, a pyridyl group, a thienyl group or a thiazolyl group, X represents a methylene group or an oxygen or sulfur atom, their enantiomers and their addition salts with a pharmaceutically acceptable base.

Among the pharmaceutically acceptable bases mention may be made, without any limitation being implied, of sodium hydroxide, potassium hydroxide, tert-butylamine, diethylamine, ethylenediamine, and the like.

The invention also extends to the process for the preparation of the compounds of formula (I). In the process for the preparation of the compounds of formula (I) in which X represents a methylene group, a sulfonyl chloride of formula (II):

in which $R_4$ has the same meaning as in the formula (I), is used as starting material, which is reacted in a basic medium:

either with a cyclohexylamine of formula (III) (prepared from the corresponding cyclohexanone by reaction, under an inert atmosphere, with benzylamine in the presence of sodium triacetoxyborohydride, followed by hydrogenolysis):

in order to lead to the compound of formula (IV):

in which $R_4$ has the same meaning as in the formula (I), or with 4-aminocyclohexanol, in order to lead to the compound of formula (V):

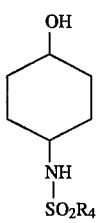 (V)

in which R₄ has the same meaning as in the formula (I), which is oxidized using Jones reagent (chromic acid in acetone and aqueous sulfuric acid), in order to lead to the compound of formula (IV) described above, which compound of formula (IV), is reacted with ethyl formate in the presence of sodium hydride, in order to lead to the compound of formula (VI):

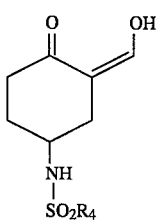 (VI)

in which R₄ has the same meaning as in the formula (I), which, depending on the nature of the compounds of formula (I) which it is desired to obtain, is subsequently subjected to the action of a carbalkoxymethylenetriphenylphosphorane which is optionally substituted at α of the ester group with a halogen atom, a linear or branched ($C_1$–$C_6$) alkyl group, a phenyl group (unsubstituted or substituted with one or more halogen atoms or linear or branched ($C_1$–$C_6$) alkyl groups, linear or branched ($C_1$–$C_6$) alkoxy groups or trihalomethyl groups), a benzyl group, a pyridylmethyl group or an imidazolylmethyl group, in order to lead to the compound of formula (VII):

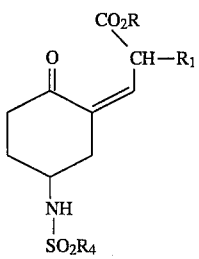 (VII)

in which $R_1$ and $R_4$ have the same meaning as in the formula (I) and R represents a group that linear or branched ($C_1$–$C_6$) alkyl, which is subsequently reacted with p-toluenesulfonic acid or trifluoroacetic acid, in order to lead to the compound of formula (VIII):

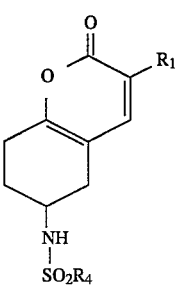 (VIII)

in which $R_1$ and $R_4$ have the same meaning as in the formula (I), which undergoes a Diels-Alder reaction with a suitably substituted alkyl 2-alkynoate, in order to lead, after possible conversions, to the compound of formula (IX):

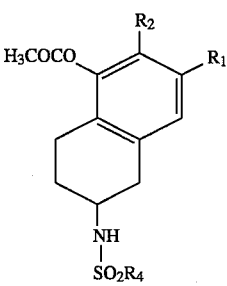 (IX)

in which $R_1$, $R_2$ and $R_4$ have the same meaning as in the formula (I), which is subjected to the action of lithium aluminum hydride in an anhydrous medium, in order to lead to the compound of formula (X):

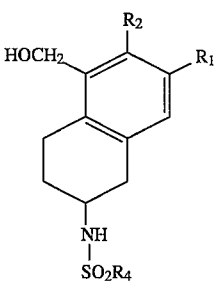 (X)

in which $R_1$, R2 and $R_4$ have the same meaning as in the formula (I), which is reacted with an oxidizing agent such as 4-benzylpyridinium dichromate, in order to lead to the aldehyde of formula (XI):

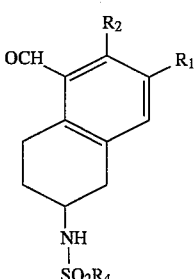 (XI)

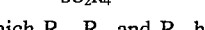

in which $R_1$, $R_2$ and $R_4$ have the same meaning as in the formula (I), which is reacted with (carbomethoxymethylene)triphenylphosphorane, in order to lead to the compound of formula (XII):

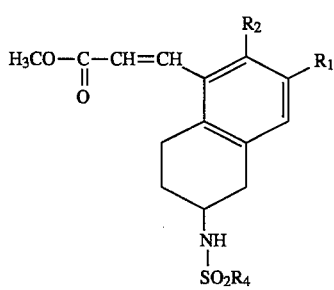

(XII)

in which $R_1$, $R_2$ and $R_4$ have the same meaning as in the formula (I), which is reduced using samarium iodide in the presence of methanol, in order to lead to the compound of formula (XIII):

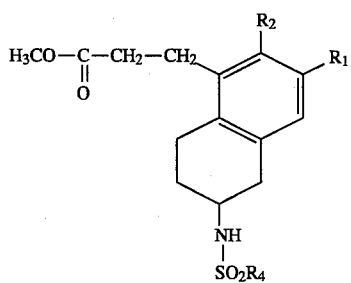

(XIII)

in which $R_1$, R2 and $R_4$ have the same meaning as in the formula (I), which is subsequently converted into the corresponding acid, ester or amide according to a standard technique of organic chemistry, in order to lead to the compound of formula (I/a), a specific case of the compounds of formula (I):

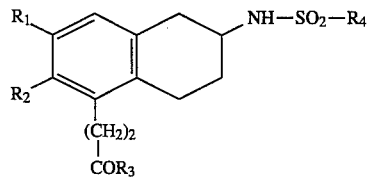

(I/a)

in which $R_1$, R2, R3 and $R_4$ have the same meaning as in the formula (I), which may, where appropriate, be purified according to a standard purification technique, the isomers of which are separated, where appropriate, according to a standard separation technique, which is converted, if so desired, into its addition salts with a pharmaceutically acceptable base.

The compound of formula (IX) described above may be obtained:

a either directly by reaction of the compound of formula (VIII) with a suitably substituted alkyl 2-alkynoate of following formula:

$R_2$—C≡C—CO$_2$R in which: R represents a linear or branched ($C_1$–$C_6$) alkyl group, and $R_2$ has the same meaning as in the formula (I), b: or, for certain values of the group $R_2$, by reaction with an alkyl 2-alkynoate of formula:

$R'_2$—C≡C—CO$_2$R in which R represents a linear or branched ($C_1$–$C_6$) alkyl group, and $R'_2$ represents a trimethylsilyl or tributylstannyl group, in order to lead, in this case, to the compound of formula (IX'):

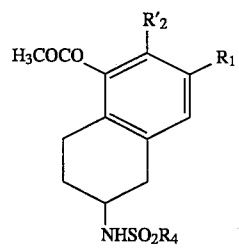

(IX')

in which $R_1$, $R_4$ and $R'_2$ have the same meaning as above, which:

when $R'_2$ is a trimethylsilyl group, is converted:
  either into the compound of formula (IX) in which $R_2$ represents a hydrogen atom,
  or into the corresponding iodo compound, which is itself subjected to the action of tetramethyltin in the presence of a metal catalyst, in order to lead to the compound of formula (IX) in which $R_2$ represents a methyl group, when $R'_2$ represents a tributylstannyl group, is converted:
  either into the compound of formula (IX) in which $R_2$ represents a bromine atom, which bromine atom may, if so desired, be substituted by a substituent $R_2$ as defined in the formula (I) in the presence of a suitable catalyst,
  or directly into the compound of formula (IX) in which $R_2$ represents a linear or branched ($C_1$–$C_6$) alkyl group or a substituted or unsubstituted phenyl group.

The compounds of formula (I), in which $R_1$ represents a benzyl, pyridylmethyl, thiazolylmethyl or imidazolylmethyl group and X represents a methylene group, are more particularly obtained from the compound of formula (XI) described above in which $R_1$ represents a bromine atom, which is reacted with the derivative of following formula:

$R_1$—Sn(C$_4$H$_9$)$_3$ leading to the suitably substituted compound of formula (XI) and then undergoing the sequence of reactions described above for the conversion of the compound of formula (XI) into the compound of formula (I/a).

When the compounds of formula (I) which it is desired to obtain are such that $R_1$ and $R_2$ each represent a hydrogen atom and X represents a methylene group, these compounds may be obtained according to the process wherein a compound of formula (XIV):

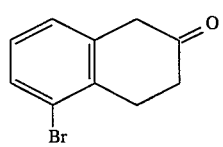

(XIV)

is used as starting material, which is reacted with an excess of methyl acrylate in the presence of a catalytic amount of palladium acetate and tri-ortho-tolylphosphine in triethylamine, in order to lead to the compound of formula (XV):

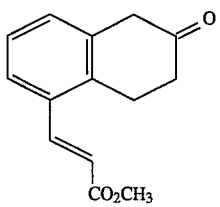

(XV)

which is convened into the compound of formula (XVI) by reaction with benzylamine in the presence of sodium triacetoxyborohydride,

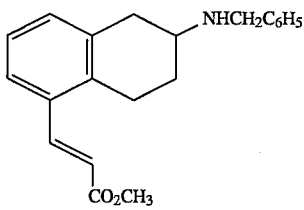

(XVI)

which undergoes a catalytic hydrogenation in order to lead to the compound of formula (XVII):

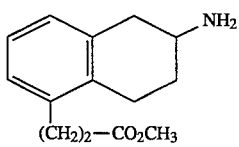

(XVII)

with which is reacted a sulfonyl chloride of formula (II) in a basic medium:

R₄SO₂Cl    (II)

in which $R_4$ has the same meaning as in the formula (I), in order to lead to the compound of formula (XVIII):

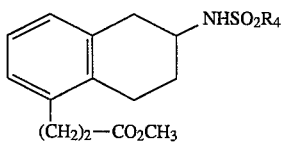

(XVIII)

in which $R_4$ has the same meaning as in the formula (I), which is subsequently converted into the corresponding acid, ester or amide according to a standard technique of organic chemistry, in order to lead to the compound of formula (I/b), a specific case of the compounds of formula (I):

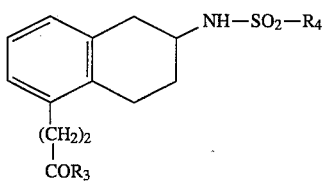

(I/b)

in which $R_3$ and $R_4$ have the same meaning as in the formula (I), which may, where appropriate, be purified according to a standard purification technique, the isomers of which may, where appropriate, be separated according to a standard separation technique, which is converted, if so desired, into its addition salts with a pharmaceutically acceptable base.

In the process for the preparation of the compounds of formula (I) in which X (=X') represents a sulfur or oxygen atom, a compound of formula (XIX):

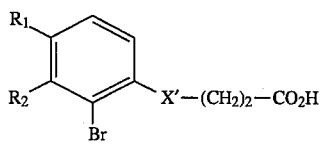

(XIX)

is used as starting material, in which $R_1$ and $R_2$ have the same meaning as in the formula (I) and X' represents a sulfur or oxygen atom, which is cyclized in the presence of polyphosphoric acid in order to lead to the compound of formula (XX):

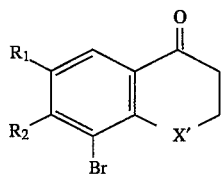

(XX)

in which $R_1$, $R_2$ and X' have the same meaning as above, which is reacted with an excess of methyl acrylate in the presence of a catalytic amount of palladium acetate and tri-ortho-tolylphosphine in triethylamine, in order to lead to the compound of formula (XXI):

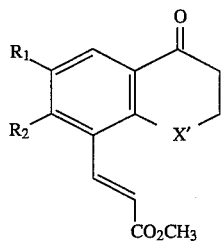

(XXI)

in which $R_1$, $R_2$ and X' have the same meaning as above, which is reacted with hydroxylamine and then with tosyl chloride, and which finally undergoes the Neber transformation in order to lead to the compound of formula (XXII):

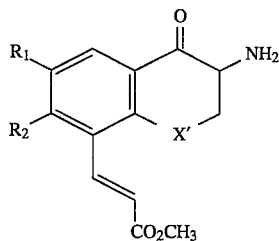

(XXII)

in which $R_1$, $R_2$ and X' have the same meaning as above, which then undergoes a reduction in the presence of a catalyst, in order to lead to the compound of formula (XXIII):

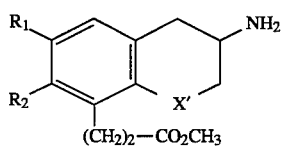

in which $R_1$, $R_2$ and X' have the same meaning as above, which is reacted with a sulfonyl chloride of formula (II) in a basic medium:

$$R_4SO_2Cl \quad (II)$$

in which $R_4$ has the same meaning as in the formula (I), in order to lead to the compound of formula (XXIV):

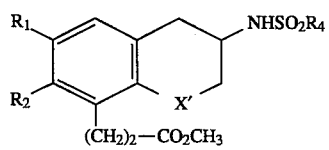

in which $R_1$, $R_2$, $R_4$ and X' have the same meaning as above, which is subsequently convened into the corresponding acid, ester or amide according to a standard technique of organic chemistry, in order to lead to the compound of formula (I/c), a specific case of the compounds of formula (I):

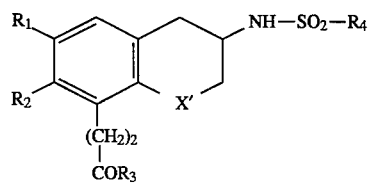

in which $R_1$, $R_2$, $R_3$, $R_4$ and X' have the same meaning as above, which may, where appropriate, be purified according to a standard purification technique, the isomers of which are separated, where appropriate, according to a standard separation technique, which is convened, if so desired, into its addition salts with a pharmaceutically acceptable base.

When the compounds of formula (I) which it is desired to obtain are such that $R_1$ represents a methyl group, $R_2$ represents a hydrogen atom and X represents a methylene group, these compounds may more particularly be obtained according to the process wherein 1,3-cyclohexanedione is used as starting material, which is reacted with tiglic aldehyde in order to lead to the compound of formula (XXV):

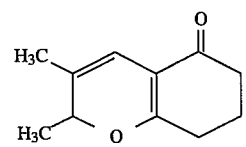

which is reacted with alkyl propiolate in order to lead to the compound of formula (XXVI):

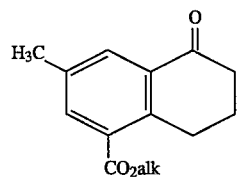

in which alk represents an alkyl group, which is reacted with hydroxylamine and then with tosyl chloride, and which finally undergoes a Neber transformation, in order to lead to the compound of formula (XXVII):

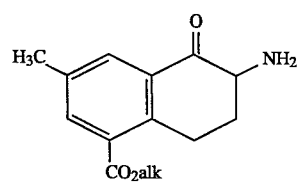

in which alk has the same meaning as above, which then undergoes a catalytic reduction, followed by the action of the sulfonyl chloride of formula (II) described above, in order to lead to the compound of formula (XXVIII):

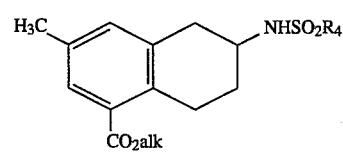

in which $R_4$ and alk have the same meaning as above, which compound of formula (XXVIII) then undergoes the sequence of reactions described above for the conversion of the compound of formula (IX) into the compound of formula (I/a) and which leads to the corresponding compound of formula (I).

The isomers of the compounds of formula (I) may be obtained by a standard separation technique at the end of the synthesis, or at any step of the synthesis which allows such a separation.

The compounds of formula (I) possess advantageous pharmacological properties. In particular, they are capable of inhibiting platelet aggregation induced by U46619 (9,11-dideoxy-11α,9α-epoxymethanoprostaglandin $F_2\alpha$), a $TXA_2$ receptor agonist, of inhibiting contractions brought about by U46619 on guinea pig trachea and of preventing in vivo bronchoconstrictions induced by U46619 in guinea pigs. In addition, the compounds inhibit the synthesis of $TXA_2$ in the blood of rabbits. The compounds of the invention possess markedly more intense pharmacological activities than those of a reference compound, BAY U3405 (Drug of the Future, 16(8), 701–705, 1991 ).

Another subject of the present invention is the pharmaceutical compositions containing as active principle at least one compound of formula (I) alone or in combination with one or more inert, non-toxic excipients or vehicles.

Among the pharmaceutical compositions according to the invention there may more particularly be mentioned those which are suitable for oral, parenteral or nasal administration, simple or sugar-coated tablets, sublingual tablets, gelatin capsules, lozenges, suppositories, creams, ointments, dermal gels, and the like.

The useful dosage varies depending on the age and weight of the patient, the nature and severity of the complaint and the route of administration. This may be an oral, nasal, rectal or parenteral route. In general, the unit dosage is graduated between 10 and 200 mg for a treatment taken 1 to 3 times per 24 hours.

The examples which follow illustrate the invention and make no limitation of it in any way. The starting materials used are known products or products prepared according to known experimental procedures. The chemical structures of the compounds described in the examples were determined according to the usual spectroscopic techniques (proton and carbon 13 nuclear magnetic resonance, mass spectrum, etc.).

EXAMPLE 1

3-{6-[(4-Chlorophenylsulfonyl)amino]-2-methyl-5,6,7,8-tetrahydronaphth-1-yl} propionic acid, sodium salt Stage A: 4,4-Diethoxy-N-benzylcyclohexylamine This compound is obtained according to the process described in Tet. Lett. 5595–5598, 1990. To 270 mmol of 4,4-diethoxycyclohexanone in 700 ml of stirred anhydrous 1,2-dichloroethane, at room temperature and under a nitrogen atmosphere, are added 270 mmol of benzylamine in 50 ml of 1,2-dichloroethane, 270 mmol of acetic acid and then 80 g of sodium triacetoxyborohydride. After stirring for 3 hours, 1 l of saturated sodium hydrogen carbonate solution is poured onto the reaction medium. The pH is brought to 8 using 1N sodium hydroxide. The organic phase is recovered, dried and evaporated. The expected product is then obtained after purification of the residual oil by chromatography on a column of silica, using a dichloromethane/methanol/aqueous ammonia (95/5/0.5) mixture as eluent.

Yield: 80%

Stage B: 4,4-Diethoxycyclohexylamine oxalate

To 200 mmol of the compound obtained in the above stage in 1.5 l of anhydrous ethanol are added dropwise 200 mmol of oxalic acid diluted in anhydrous ethanol, followed by 6.1 g of palladium on charcoal. The reaction medium is hydrogenated for 5 hours at 45° C. under a pressure of hydrogen. After filtration of the catalyst, the expected product is obtained in solid form after evaporation.

Yield: 90%

Elemental microanalysis:

|  | C % | H % | N % |
| --- | --- | --- | --- |
| calculated | 51.97 | 8.36 | 5.05 |
| found | 51.58 | 8.26 | 5.28 |

Stage C: 4-(4-Chlorophenylsulfonyl)aminocyclohexanone

To a solution containing 36 mmol of 4-chlorophenylsulfonyl chloride in 100 ml of tetrahydrofuran (THF) are added 18 mmol of the compound obtained in the above stage in 100 ml of water, as well as a 1N potassium hydroxide solution, in order to maintain the pH at 9. After stirring for 90 minutes, the reaction medium is treated with 1N hydrochloric acid until the pH is 3, diluted with 50 ml of water and then extracted with ether. The ether phase is then dried and evaporated. The expected product is then obtained by purification of the residual solid by chromatography on a column of silica, using a cyclohexane/ethyl acetate (70/30) mixture as eluent.

Yield: 82 %

Stage D: 4-(4-Chlorophenylsulfonyl)amino-2-hydroxymethylenecyclohexanone

This compound is obtained according to the process described in Synthesis, 796–797, 1983. To 78 mmol of sodium hydride (washed with anhydrous pentane) diluted in anhydrous THF are added dropwise, under nitrogen, 195 mmol of ethyl formate in 25 ml of THF, followed by dropwise addition of 19 mmol of the compound obtained in the above stage in 40 ml of THF. The stirring is maintained for 90 minutes. After dilution of the medium with water and addition of hydrochloric acid until the pH is 4, the expected product is extracted with ether and is obtained after drying and evaporation of the ether phase.

Stage E: Methyl 3-[5-(4-chlorophenylsulfonyl)amino-2-oxocyclohexylidene]propanoate 20 mmol of the compound obtained in the above stage and 23 mmol of (carbomethoxymethylidene)triphenylphosphorane are mixed in 200 ml of anhydrous chloroform. The mixture is brought to reflux for two hours. After cooling and evaporation of the solvent, the expected product is obtained.

Stage F: 6-(4-Chlorophenylsulfonyl)amino-2-oxo-5,6,7,8-tetrahydro-2H-benzo[e]pyran This compound is obtained according to the process described in Tetrahedron, 24(7), 2851–2858, 1968. 22 mmol of p-toluenesulfonic acid dissolved in 315 ml of anhydrous toluene are placed in a three-necked flask fitted with a Dean-Stark apparatus and the mixture is brought to reflux for 45 minutes. The Dean-Stark apparatus is then removed and 20 mmol of the compound obtained in the above stage in 150 ml of anhydrous toluene are added to the mixture, which is brought to reflux for 4 hours. The medium is then diluted with water. After extraction with ether, drying and evaporation, the expected product is obtained in solid form after purification of the residue by chromatography on a column of silica, using a cyclohexane/ethyl acetate (50/50) mixture as eluent.

Melting point: 215° C.

Stage G: Methyl 6-(4-chlorophenylsulfonyl)amino-2-methyl-5,6,7,8-tetrahydronaphthalene-1-carboxylate 22 mmol of the compound obtained in the above stage are placed in an autoclave with 12.4 ml of methyl 2-butynoate and the mixture is brought to 170° C. for 48 hours. The expected product is then obtained after purification by chromatography on a column of silica, using a cyclohexane/ethyl acetate (80/20) mixture as eluent.

Stage H: 6-(4-Chlorophenylsulfonyl)amino-2-methyl-1-hydroxy-methyl-5,6,7,8-tetrahydronaphthalene 19 mmol of lithium aluminum hydride are placed in 50 ml of anhydrous THF with stirring. 9.5 mmol of the compound described in the above stage in 20 ml of THF are then added and the mixture is stirred for one hour. After addition of 5 ml of methanol and then 20 ml of water, the expected product is obtained after extraction with ether, drying and evaporation.

Stage I: 6-(4-Chlorophenylsulfonyl)amino-2-methyl-5,6,7,8-tetrahydronaphthalene-1-carboxaldehyde This compound is obtained according to the process described in Synthesic Communications 21(3), 419–425, 1991. 440 mmol of 4-benzylpyridinium dichromate are placed in 225 ml of dichloromethane with stirring. 7 mmol of the compound obtained in the above stage in 10 ml of dichloromethane are then added and the mixture is stirred for one hour at room temperature. 200 ml of an ether/hexane (1/1) mixture are added to the mixture. The precipitate formed is filtered off. The filtrates are recovered and evaporated, and the expected product is obtained after purification of the residue by chromatography on a column of silica, using a cyclohexane/ethyl acetate (80/20) mixture as eluent.

Stage J: Methyl 3-[6-(4-chlorophenylsulfonyl)amino-2-methyl-5,6,7,8-tetrahydronaphth-1-yl]- 2-propenoate 4 mmol of the compound obtained in the above stage are brought to reflux for 48 hours in 120 ml of chloroform, in the presence of 5.2 mmol of (carbomethoxymethylidene)triphenylphosphorane. The solvents are evaporated off and the expected product is obtained after purification of the residue by chromatography on a column of silica, using a cyclohexane/ethyl acetate (60/40) mixture as eluent.

Stage K: Methyl 3-[6-(4-chlorophenylsulfonyl)amino-2-methyl-5,6,7,8-tetrahydronaphth-1-yl] propanoate This compound is obtained according to the process described in J.A.C.S., 2693–2698, 1980. To 165 ml of 0.1N samarium iodide solution in THF, placed under an argon atmosphere and with stirring, are added 1.1 mmol of the compound obtained in the above stage. The mixture is stirred for 30 minutes at room temperature. After addition of 0.5 ml of methanol, the mixture is stirred for an additional 30 minutes. After treating with 200ml of 0.1N hydrochloric acid solution and extraction with ether, the combined organic phases are washed with water, then with saturated sodium thiosulfate solution and again with water. After drying and evaporation, the expected product is obtained.

Stage L: 3-{6-[(4-Chlorophenylsulfonyl)amino]-2-methyl-5,6,7,8-tetrahydronaphth-1-yl } propionic acid, sodium salt 1 mmol of the compound obtained in the above stage is brought to reflux in 10 ml of methanol, in the presence of 3 equivalents of 2N sodium hydroxide, for one hour. After cooling, the mixture is acidified with 1N hydrochloric acid and, after extraction with ethyl acetate, drying and evaporation, the residue is taken up in 5 ml of methanol and is treated with one equivalent of 1N sodium hydroxide. The expected product is then obtained after evaporation of the solvent. The purity is verified by HPLC and the proton nuclear magnetic resonance spectrum, acquired in DMSO-$d_6$ in the presence of TMS, confirms the structure of the product.

EXAMPLE 2

3-{6-[(4-Chlorophenylsulfonyl)amino]-2,3-dimethyl-5,6,7,8-tetrahydronaphth-1-yl} propionic acid, sodium salt Stages A to D:

These stages are identical to Stages A to D of Example 1.

Stage E:- Methyl 2-methyl-3-[5-(4-chlorophenylsulfonyl)amino-2-oxocyclohexylidene]propanoate The expected product is obtained according to the process described in Stage E of Example 1, replacing (carbomethoxymethylidene)triphenylphosphorane by (carbethoxyethylidene) triphenylphosphorane.

Stage F: 6-(4-Chlorophenylsulfonyl)amino-3-methyl-2-oxo-4a,5,6,7,8,8a-hexahydro-2H-benzo[e]pyran The expected product is obtained by working as in Stage F of Example 1, using the compound obtained in the above stage.

Stage G: Methyl 6-(4-chlorophenylsulfonyl )amino-2,3-dimethyl-5,6,7,8-tetrahydronaphthalene-1-carboxylate The experimental procedure is identical to that described in Stage G of Example 1.

Stage H: 6-(4-Chlorophenylsulfonyl)amino-2,3-dimethyl-1-hydroxy- methyl-5,6,7,8- tetrahydronaphthalene The experimental procedure is identical to that described in Stage H of Example 1.

Stage I: 6-(4-Chlorophenylsulfonyl)amino-2,3-dimethyl-5,6,7,8-tetrahydronaphthalene-1-carboxaldehyde The experimental procedure is identical to that described in Stage I of Example 1.

Stage J: Methyl 3-[6-(4-chlorophenylsulfonyl)amino-2,3-dimethyl-5,6,7,8-tetrahydronaphth-1-yl]-2-propenoate The experimental procedure is identical to that described in Stage J of Example 1.

Stage K: Methyl 3-[6-(4-chlorophenylsulfonyl)amino-2,3-dimethyl-5,6,7,8-tetrahydronaphth-1-yl]propanoate The experimental procedure is identical to that described in Stage K of Example 1.

Stage L: 3-{6-[(4-Chlorophenylsulfonyl)amino]-2,3-dimethyl-5,6,7,8-tetrahydronaphth-1-yl } propionic acid, sodium salt The experimental procedure is identical to that described in Stage L of Example 1. The purity of the expected product is verified by HPLC and the proton nuclear magnetic resonance (NMR) spectrum, acquired in DMSO in the presence of TMS, confirms the structure of the product.

EXAMPLE 3

3-{6-[(4-Fluorophenylsulfonyl)amino]-2-methyl-5,6,7,8-tetrahydronaphth-1-yl} propionic acid, sodium salt The expected product is obtained according to the process described in Example 1, replacing in Stage C 4-chlorophenylsulfonyl chloride by 4-fluorophenylsulfonyl chloride. The purity and the structure of the expected product are verified by HPLC and NMR.

Elemental microanalysis:

|  | C % | H % | N % | S % |
|---|---|---|---|---|
| calculated | 58.10 | 5.12 | 3.39 | 7.76 |
| found | 58.12 | 5.62 | 3.54 | 7.91 |

EXAMPLE 4

3-{6-[(4-Chlorophenylsulfonyl)amino]-2-propyl-5,6,7,8-tetrahydronaphth-1-yl } propionic acid The expected product is obtained in free acid form according to the process described in Example 1, replacing in Stage G methyl 2-butynoate by methyl 2-hexynoate. The purity and the structure of the expected product are verified by HPLC and NMR.

Melting point: 165°–167° C. Elemental microanalysis:

|  | C % | H % | N % | Cl % | S % |
|---|---|---|---|---|---|
| calculated | 60.61 | 6.01 | 3.21 | 8.13 | 7.35 |
| found | 61.03 | 6.27 | 3.24 | 8.54 | 7.19 |

EXAMPLE 5

3-{6-[(4-Chlorophenylsulfonyl)amino]-3-chloro-2-methyl-5,6,7,8-tetrahydronaphth- 1-yl}propionic acid, sodium salt Stage A: 4-(4-Chlorophenylsulfonyl)aminocyclohexanol To 100 g of trans-4-aminocyclohexanol hydrochloride suspended in 1l of chloroform are added, at 5° C., 184 ml of triethylamine, followed by a solution containing 143 g of 4-chlorophenylsulfonyl chloride in 150 ml of chloroform. After reaction for 2 hours, the reaction mixture is poured onto 500 ml of water. The expected product is obtained by filtration of the precipitate.

Yield: 95%

Melting point: 138°–142° C.

Stage B: 4-(4-(Chlorophenylsulfonyl)aminocyclohexanone

To 182 g of the compound obtained in the above stage dissolved in 1.2 l of acetone are added, with vigorous stirring and at a temperature not exceeding 35° C., 150 ml of an oxidizing solution obtained by dissolving 80 g of chromium trioxide in 190 ml of water and 70 ml of pure sulfuric acid. After stirring for one hour, the precipitate formed is filtered off and rinsed with acetone. The filtrates are diluted with 250 ml of isopropyl alcohol and the pH of the solution is brought to 7 using sodium hydrogen carbonate. After filtration and evaporation of the solvents, the residue is taken up in dichloromethane. The organic phase is washed with 1N hydrochloric acid, 1N sodium hydroxide and then with water. After drying and evaporation, the expected product is obtained.

Yield: 70%

Melting point: 103°–105° C.

Stages C to K:

Stages C to K are identical to Stages D to L of Example 1, but in Stage D (carbomethoxymethylene)triphenylphosphorane is replaced by (carbomethoxychloromethylene)triphenylphosphorane. The purity and the structure of the expected product are verified by HPLC and NMR.

EXAMPLE 6

3-{6-[(4-Chlorophenylsulfonyl)amino]-5,6,7,8-tetrahydronaphth-1-yl}propionic acid, sodium salt Stage A: 5-Bromo-2-oxo-1,2,3,4-tetrahydronaphthalene 1.12 mmol of an aluminum chloride are placed in 1.5 l of anhydrous methylene chloride. 279 mmol of phenylacetyl chloride in 100 ml of dichloromethane are added at a temperature between −5° C. and −10° C. After stirring for one hour, ethylene is bubbled through at this temperature for 2 hours 30 minutes. 1 l of water is then added slowly. The organic phase is separated out after settling of the phases has taken place, dried and evaporated. The expected product is then obtained after purification by chromatography on a column of silica, using a cyclohexane/ether (95/5) mixture as eluent.

Melting point: 62° C.

Stage B: Methyl 3-(6-oxo-5,6,7,8-tetrahydronaphth-1-yl)-2-propenoate 31 mmol of the compound obtained in the above stage are placed in 15 ml of triethylamine in the presence of 38 mmol of methyl acrylate, 70 mg of palladium diacetate and 370 mg of tri-ortho-tolylphosphine. The mixture is brought to 100° C. for 10 hours in an autoclave. After addition of 300 ml of 1N hydrochloric acid, extraction with dichloromethane, drying and evaporation, the expected product is obtained after purification of the residue by chromatography on a column of silica, using a cyclohexane/ethyl acetate (70/30) mixture as eluent.

Stage C: Methyl 3-(6-benzylamino-5,6,7,8-tetrahydronaphth-1-yl)-2-propenoate 14.7 mmol of the compound obtained in the above stage are dissolved in 45 ml of 1,2-dichloroethane. 14.7 mmol of benzylamine dissolved in 3 ml of 1,2-dichloroethane and 58.8 mmol of acetic acid are then successively added. After stirring the reaction medium for 45 minutes, 82 mmol of sodium triacetoxyborohydride are added. After 15 h, the reaction medium is treated with saturated sodium hydrogen carbonate solution and then with 1N sodium hydroxide until the pH is 8. After separation of the phases once settling has taken place and evaporation of the solvents, the crude product is purified by chromatography, using a cyclohexane/ethyl acetate (60/40) mixture as eluent.

Yield: 86%

Stage D: Methyl 3-[6-amino-5,6,7,8-tetrahydronaphth-1-yl] propanoate hydrochloride 12.6 mmol of the compound obtained in the above stage are dissolved in ethanol. 12.6 mmol of hydrochloric acid dissolved in ethanol are subsequently added, followed by 200 mg of palladium on charcoal. The medium is brought to 50° C. and then subjected to the action of hydrogen. After 48 h, the palladium is filtered off and the solvents are then evaporated off.

Stage E: Methyl 3-[6-(4-chlorophenylsulfonyl)amino-5,6,7,8-tetrahydronaphth-1-yl]propanoate The compound obtained in the above stage is subjected to a sulfonylation reaction according to the process described in Stage A of Example 5. The product is purified by chromatography on a column of silica, using a cyclohexane/ethyl acetate (80/20) mixture as eluent.

Stage F: 3-{6-[(4-Chlorophenylsulfonyl)amino]-5,6,7,8-tetrahydronaphth-1-yl }propionic acid, sodium salt The expected product is obtained according to the process described in Stage L of Example 1.

Elemental microanalysis:

|  | C % | H % | N % | Cl % | S % |
|---|---|---|---|---|---|
| calculated | 54.88 | 4.61 | 3.37 | 8.52 | 7.71 |
| found | 55.19 | 4.76 | 3.54 | 8.66 | 7.08 |

EXAMPLE 7

3-{6-[(4-Chlorophenylsulfonyl)amino ]-2-methyl-5,6,7,8-tetrahydronaphth-1-yl } propionic acid The compound of Example 1 in free acid form may also be obtained according to the following process:

Stages A and B:

These stages are identical to Stages A and B of Example 5.

Stages C, D and E:

These stages are identical to Stages D, E and F of Example 1.

Stage F: Ethyl 6-(4-chlorophenylsulfonyl)amino-2-trimethylsilyl-5,6,7,8-tetrahydronaphthalene-1-carboxylate 69 mmol of the compound obtained in the above stage and 276 mmol of ethyl trimethylsilylpropynoate are heated to 180° C. in the presence of 150 ml of decalin for 72 h. After cooling and evaporation of the decalin, the crude product is chromatographed on a column of silica, using a cyclohexane/ethyl acetate (80/20) mixture as eluent.

Yield: 72%

Stage G: Ethyl 6-(4-chlorophenylsulfonyl)amino-2-iodo-5,6,7,8-tetrahydronaphthalene-1-carboxylate The expected product is obtained according to the process described in Angew. Chem. Int., 7, 488–489, 1977.46 mmol of the compound obtained in the above stage dissolved in 300 ml of dichloromethane are placed together with 46 mmol of ICl (1M solution in dichloromethane). After 1 h 30, the solvents are evaporated off and the crude product is chromatographed on a column of silica, using a cyclohexane/ethyl acetate (80/20) mixture as eluent.

Yield: 85%

Stage H: Ethyl 6-(4-chlorophenylsulfonyl)amino-2-methyl-5,6,7,8-tetrahydronaphthalene-1-carboxylate The expected product is obtained according to the process described in Tet. Lett., 33, 17, 2413–2416, 1992. To 39 mmol of the compound obtained in the above stage in 200 ml of N-methylpyrrolidone are successively added 196 mmol of tetramethyltin and then 2 mmol of tetrakis- (triphenylphosphine)palladium. The reaction medium is brought to 110° C. for 8 h. The solvents are subsequently evaporated off and the crude product is chromatographed on a column of silica, using a cyclohexane/ethyl acetate (80/20) mixture as eluent.

Yield: 95%

Stages I, J, K and L:

These stages are identical to Stages H, I, J and K of Example 1.

Stage M: 3-[6-(4-Chlorophenylsulfonyl)amino-2-methyl-5,6,7,8-tetrahydronaphth-1-yl]propionic acid 30 mmol of the product obtained in the above stage are dissolved in 10 ml of methanol in the presence of 90 mmol of aqueous 1N sodium hydroxide solution. The reaction medium is brought to reflux for 30 minutes and is then acidified with 1N hydrochloric acid. The expected product is then extracted with ethyl acetate and the solvents are evaporated off.

Melting point: 203° C.

Elemental microanalysis:

|  | C % | H % | N % | Cl % | S % |
| --- | --- | --- | --- | --- | --- |
| calculated | 58.89 | 5.44 | 3.43 | 8.69 | 7.86 |
| found | 58.63 | 5.39 | 3.58 | 8.87 | 7.53 |

EXAMPLES 7a and 7b

α and β isomers of the compound of Example 7

Stages A to H are identical to Stages A to H of Example 7.

Stage I: Ethyl 6-amino-2-methyl-5,6,7,8-tetrahydronaphthalene-1-carboxylate 13 mmol of the compound obtained in the above stage dissolved in 50 ml of DMPU and 100 ml of tetrahydrofuran are treated with 80 mmol of samarium iodide at reflux for 5 hours. After evaporation of the solvents, the product is bound to a sulfonic acid resin, washed with water and then eluted out with aqueous ammonia. The two enantiomers obtained are subsequently separated in a conventional manner using a chiral acid. The acid salt is then eluted out. Each enantiomer then undergoes the following sequence of reactions:

Stage J: Ethyl 6-(4-chlorophenylsulfonyl)amino-2-methyl-5,6,7,8-tetrahydronaphthalene-1-carboxylate, α isomer and β isomer The experimental procedure used is identical to that of Stage A of Example 5.

Stages K, L, M and N:

These stages are identical to Stages H, I, J and K of Example 1.

Stage O:

This stage is identical to Stage M of Example 7.

EXAMPLE 8

3-[6-(1-Naphthylsulfonylamino)-2-methyl-5,6,7,8-tetrahydronaphth-1-yl]propionic acid Stage A: 4-(1-Naphthylsulfonylamino)cyclohexanol To 18.6 g of trans-4-aminocyclohexanol hydrochloride suspended in 700 ml of chloroform are added, at 5° C., 34 ml of triethylamine, followed by a solution containing 18.6g of 1-naphthylsulfonyl chloride in 100 ml of chloroform. After reacting for 15 hours, the reaction mixture is poured onto 500 ml of water. The expected product is obtained by filtration of the precipitate.

Yield: 89%

Melting point: 174° C.

Stage B: 4-(1-Naphthylsulfonylamino)cyclohexanone

The experimental procedure used is identical to the experimental procedure of Stage B of Example 5.

Yield: 94%

Stages C, D and E:

The products expected in these stages are obtained according to the processes described in Stages D, E and F of Example 1.

Stage F: Methyl 6-(1-naphthylsulfonyl)amino-2-methyl-5,6,7,8-tetrahydronaphthalene-1-carboxylate To 11.8 mmol of the compound obtained in Stage E in 100 ml of decalin are added 48 mmol of methyl butynoate. The reaction medium is heated in an autoclave at 270° C. for 6 h. The product is purified by chromatography on a column of silica, using a cyclohexane/ethyl acetate (80/20) mixture as eluent.

Stages G, H, I, J and K:

The products expected in these stages are obtained according to the processes described in Stages I, J, K, L and M of Example 7.

The expected 3-[6-(1-naphthylsulfonylamino)-2-methyl-5,6,7,8-tetrahydronaphth-1-yl]propionic acid is analysed by proton nuclear magnetic resonance, dissolved in $CDCl_3$. Its purity is verified by HPLC.

Elemental microanalysis:

|  | C % | H % | N % | S % |
| --- | --- | --- | --- | --- |
| calculated | 68.06 | 5.95 | 3.31 | 7.57 |
| found | 67.50 | 6.13 | 3.39 | 7.83 |

EXAMPLE 9

3-[6-(4-Tolylsulfonylamino)-5,6,7,8-tetrahydronaphth-1-yl]propionic acid

Stages A, B, C and D are identical to Stages A, B, C and D of Example 6.

Stage E: Methyl 3-[6-(4-tolylsulfonylamino)-5,6,7,8-tetrahydronaphth-1-yl]propanoate The expected product is obtained according to the experimental procedure described in Stage E of Example 6, replacing sulfonyl chloride by para-toluenesulfonyl chloride.

Stage F: 3-[6-(4-Tolylsulfonylamino)-5,6,7,8-tetrahydronaphth-1-yl]propionic acid The expected product is obtained according to the process described in Stage M of Example 7.

Elemental microanalysis:

|  | C % | H % | N % | S % |
|---|---|---|---|---|
| calculated | 64.32 | 6.21 | 3.75 | 8.59 |
| found | 64.67 | 6.29 | 3.84 | 8.63 |

EXAMPLE 10

3-{6-[(4-Chlorophenylsulfonyl)amino]-3-methyl-5,6,7,8-tetrahydronaphth-1-yl} propionic acid Stage A: 2,3-Dimethyl-5,6,7,8-tetrahydrochrom-3-en-5-one The expected product is obtained in oil form according to the process described in Tet. Lett., 39, 3407, 1975 by reaction of 0.99 mol of 1,3-cyclohexanedione and 1.19 mol of tiglic aldehyde in pyridine.

Elemental microanalysis:

|  | C % | H % |
|---|---|---|
| calculated | 74.13 | 7.92 |
| found | 73.97 | 7.71 |

Stage B: Ethyl 3-methyl-5-oxo-5,6,7,8-tetrahydronaphthalene-1-carboxylate

The expected product is obtained from the compound described in the above stage and ethyl propiolate according to the process described in J. Org. Chem., 41, 2918, 1976.

Elemental microanalysis:

|  | C % | H % |
|---|---|---|
| calculated | 72.39 | 6.94 |
| found | 71.97 | 6.77 |

Stage C: Ethyl 3-methyl-5-hydroxyimino-5,6,7,8-tetrahydronaphthalene-1-carboxylate The expected product is obtained according to the process described in J. Med. Chem., 863, 1972 from the compound obtained in the above stage and hydroxylamine.

Stage D: Ethyl 3-methyl-5-tosyloxyimino-5,6,7,8-tetrahydronaphthalene-1-carboxylate The expected product is obtained according to the process described in J. Med. Chem., 863, 1972 from the compound described in the above stage and tosyl chloride.

Stage E: Ethyl 3-methyl-5-oxo-6-amino-5,6,7,8-tetrahydronaphthalene-1-carboxylate, hydrochloride To 142 mmol of sodium dissolved in 66 ml of ethanol and 730 ml of benzene are added 150 mmol of the compound obtained in the above stage. After stirring for 20 hours at room temperature, the precipitate is filtered off and rinsed with ether. The organic phases are combined and extracted with 10% hydrochloric acid. After evaporation of the aqueous phases, the expected product is obtained in the form of a solid, which is rinsed with an ethanol/ether (50/50) mixture.

Stage F: Ethyl 6-(4-chlorophenylsulfonyl)amino-3-methyl-5,6,7,8-tetrahydro-naphthalene-1-carboxylate 35 mmol of the compound obtained in the above stage are hydrogenated in 80 ml of acetic acid in the presence of 3 g of 10% palladium hydroxide on charcoal. After absorption of one equivalent of hydrogen, 3 ml of 70% perchloric acid are added and the hydrogenolysis is continued. The catalyst is then filtered off and 2.1 g of potassium acetate in 20 ml of acetic acid are added to the filtrate. After filtration of the precipitate, the filtrate is evaporated. The residue obtained is then amidated by addition of 35 mmol of 4-chlorophenylsulfonyl chloride in chloroform in the presence of 70 mmol of triethylamine. After evaporation, the oil obtained is purified by chromatography on a column of silica, using a dichloromethane/methanol (99/1) mixture as eluent.

Stage G: 6-(4-Chlorophenylsulfonyl)amino-3-methyl-1-hydroxymethyl-5,6,7,8-tetrahydronaphthalene The expected product is obtained according to the process described in Stage H of Example 1.

Stage H: 6-(4-Chlorophenylsulfonyl)amino-3-methyl-5,6,7,8-tetrahydro-naphthalene-1-carboxaldehyde The expected product is obtained according to the process described in Stage I of Example 1.

Stage I: Methyl 3-[6-(4-chlorophenylsulfonyl)amino-3-methyl-5,6,7,8-tetrahydronaphth-1-yl]-2-propenoate The expected product is obtained according to the process described in Stage J of Example 1.

Stage J: Methyl 3-[6-(4-chlorophenylsulfonyl)amino-3-methyl-5,6,7,8-tetrahydronaphth-1-yl] propanoate The expected product is obtained according to the process described in Stage K of Example 1.

Stage K: 3-{6-[(4-Chlorophenylsulfonyl)amino]-3-methyl-5,6,7,8-tetrahydronaphth-1-yl} propionic acid The expected product is obtained according to the process described in Stage M of Example 7.

Melting point: 170°–173° C.

Elemental microanalysis:

|  | C % | H % | N % | Cl % | S % |
|---|---|---|---|---|---|
| calculated | 58.89 | 5.44 | 3.43 | 8.69 | 7.88 |
| found | 58.84 | 5.50 | 3.50 | 8.69 | 7.80 |

EXAMPLE 11

3-{6-[(4-Fluorophenylsulfonyl)amino]-3-methyl-5,6,7,8-tetrahydronaphth-1-yl} propionic acid The expected product is obtained according to the process described in Example 10, replacing in Stage F 4-chlorophenylsulfonyl chloride by 4-fluorophenylsulfonyl chloride.

Melting point: 174°–176° C.

Elemental microanalysis:

|  | C % | H % | N % | S % |
|---|---|---|---|---|
| calculated | 61.37 | 5.66 | 3.58 | 8.19 |
| found | 61.57 | 5.71 | 3.64 | 7.92 |

EXAMPLE 12

3-{6-[(4-Chlorophenylsulfonyl)amino]-2-phenyl-5,6,7,8-tetrahydronaphth-1-yl} propionic acid Stages A to F:

These stages are identical to Stages A to F of Example 1.

Stage G: Methyl 6-(4-chlorophenylsulfonyl)amino-2-tributylstannyl-5,6,7,8-tetrahydro-naphthalene-1-carboxylate The expected product is obtained according to the process described in Stage G of Example 1, replacing methyl 2-butynoate by methyl 3-tributylstannylpropynoate.

Stage H: Methyl 6-(4-chlorophenylsulfonyl)amino-2-phenyl-5,6,7,8-tetrahydro-naphthalene-1-carboxylate To 1 g of the compound obtained in the above stage dissolved in 20 ml of N-methylpyrrolidone are successively added 750 ml of bromobenzene and 80 mg of tetrakis(triphenylphosphine)palladium. The reaction medium is brought to 110° C. for 16 hours. After evaporation of the solvent and chromatography on a column of silica, using a cyclohexane/ethyl acetate (80/20) mixture as eluent, the expected product is obtained.

Stages I to M:

These stages are identical to Stages I to M of Example 7 and lead to the title product.

Melting point: 98°–100° C.

Elemental microanalysis:

|  | C % | H % | N % | Cl % | S % |
| --- | --- | --- | --- | --- | --- |
| calculated | 63.89 | 5.15 | 2.98 | 7.54 | 6.82 |
| found | 63.61 | 5.15 | 3.03 | 8.45 | 6.43 |

EXAMPLE 13

3-{6-[(4-Chlorophenylsulfonyl)amino]-2-isopropyl-5,6,7,8-tetrahydronaphth-1-yl}propionic acid The expected product is obtained according to the process described in Example 1, replacing methyl 2-butynoate by methyl 4-methyl-2-pentynoate. The free acid is obtained directly in Stage L by extraction with ethyl acetate.

Melting point: 167°–169° C.

Elemental microanalysis:

|  | C % | H % | N % | Cl % | S % |
| --- | --- | --- | --- | --- | --- |
| calculated | 60.61 | 6.01 | 3.21 | 8.13 | 7.35 |
| found | 60.60 | 5.95 | 3.30 | 8.20 | 6.76 |

EXAMPLE 14

3-{6-[(4-Chlorophenylsulfonyl)amino]-3-(3-pyridinyl)methyl-5,6,7,8-tetrahydronaphth-1yl}propionic acid Stages A to F are identical to Stages A to F of Example 1.

Stage G: 3-Bromo-6-(4-chlorophenylsulfonyl)amino-2-oxo-5,6,7,8-tetrahydro-2H-benzo[e]pyran The expected product is obtained according to the process described in Synthesis, 34 (8), 2239–2244, 1969. 50 g of the compound obtained in Stage F are suspended in 500 ml of acetic acid. The mixture is stirred vigorously and 8 ml of bromine are added. After stirring for 4 hours at room temperature, the solvent is evaporated off. The residue is purified by chromatography on a column of silica, with a cyclohexane/ethyl acetate (50/50) mixture as eluent.

Melting point: 168°–170° C.

Stage H: Methyl 3-bromo-6-(4-chlorophenylsulfonyl)amino-5,6,7,8-tetrahydronaphthalene-1-carboxylate 5 g of the compound obtained in the above stage are placed in an autoclave with 5 ml of methyl propynoate and 80 ml of decalin, and the mixture is brought to 200° C. for 16 hours. The expected product is then obtained after purification by chromatography on a column of silica, using a cyclohexane/ethyl acetate (80/20) mixture as eluent.

Stage I: 3-Bromo-6-(4-chlorophenylsulfonyl)amino-1-hydroxymethyl-5,6,7,8-tetrahydronaphthalene The expected product is obtained according to the process described in Stage H of Example 1.

Stage J: 3-Bromo-6-(4-chlorophenylsulfonyl)amino-5,6,7,8-tetrahydronaphthalene-1-carboxaldehyde The experimental procedure is identical to that described in Stage I of Example 1.

Stage K: 6-(4-Chlorophenylsulfonyl)amino-3-(3-pyridinyl)methyl-5,6,7,8-tetrahydronaphthalene-1-carb oxaldehyde To 1.57 g of the compound obtained in the above stage dissolved in 10 ml of N-methylpyrrolidone are successively added 3.75 g of 3-tributylstannylmethylpyridine and 0.4 g of tetrakis(triphenylphosphine)palladium. The reaction medium is brought to 110° C. for 7 hours. After evaporation of the solvent and chromatography on a column of silica, with a cyclohexane/ethyl acetate (40/60) mixture as eluent, the expected product is obtained.

Stage L: Methyl 3-[6-(4-chlorophenylsulfonyl )amino-3-(3-pyridyl)methyl-5,6,7,8-tetrahydronaphth-1yl]-2-propenoate To 930 mg of the compound obtained in the above stage dissolved in 25 ml of dichloromethane are added 800 mg of (carbomethoxymethylidene)triphenylphosphorane. After 48 hours at room temperature, the solvent is evaporated off and the expected product is obtained after purification by chromatography on a column of silica, using a cyclohexane/ethyl acetate (50/50) mixture as eluent.

Stage M: Methyl 3-[6-(4-chlorophenylsulfonyl)amino-3-(3-pyridyl)methyl-5,6,7,8-tetrahydronaphth-1yl]propanoate To 800 mg of the compound obtained in the above stage dissolved in 20 ml of methanol are successively added, at room temperature, 95 mg of cobalt chloride hexahydrate and then, portionwise, 121 mg of sodium borohydride. After stirring for 2 hours, the solvent is evaporated off. The expected product is purified on a column of silica, using a cyclohexane/ethyl acetate (50/50) mixture as eluent.

Stage N: 3-{6-[(4-Chlorophenylsulfonyl)amino]-3-(3-pyridyl)methyl-5,6,7,8-tetrahydronaphth-1yl]prop ionic acid To 610 mg of the product obtained in the above stage dissolved in 50 ml of methanol are added 4 ml of 1N sodium hydroxide. The mixture is brought to reflux for 2 hours. After cooling the solution, acetic acid is added until the pH =6. The expected product is then obtained by filtration.

EXAMPLE 15

3-{6-[(4-Chlorophenylsulfonyl)amino]-2-methyl-3(3-pyridinyl)methyl-5,6,7,8-tetrahydro naphth-1yl}propionic acid The expected product is obtained according to the process described in Example 14, replacing in Stage H methyl propynoate by methyl 2-butynoate.

EXAMPLE 16

3-[3-(4-Chlorophenylsulfonyl)amino-8-chromanyl]propionic acid

Stage A: 3-(2-Bromophenoxy)propionic acid 1 mol of the potassium salt of 3-bromopropionic acid and 1 mol of potassium 2-bromophenate are brought to reflux in 1 liter of ethanol and 200 ml of water. After the solvents have been evaporated off and the residue taken up in water, the pH is brought to 7.2. The aqueous phase is washed with ethyl acetate and acidified, and the expected product is obtained by filtration of the precipitate formed.

Stage B: 3-Bromo-4-chromanone 326 mmol of the compound obtained in the above stage are heated at 100° C. in the presence of 500 g of polyphosphonic acid. 1.5 kg of ice are then added to the mixture and, after extraction with ethyl acetate and evaporation, the expected product is obtained.

Melting point: 48°–51 ° C.

Stage c: Methyl 3-(4-oxochroman-8-yl)-2-propenoate 20 mmol of the compound obtained in the above stage, 24.5 ml of methyl acrylate, 300 ml of triethylamine, 0.6 g of palladium acetate and 10 mmol of tri-ortho-tolyl phosphine are brought to 100° C. for 10 h. After concentration under vacuum, the residue is taken up in dichloromethane. The organic phase is washed with 1N hydrochloric acid, then with water and evaporated, and leads to the expected product.

Stages D, E and F:

These stages are identical to Stages C, D and E of Example 10 and lead to methyl 3-(3 - amino-4-oxochroman-8-yl)-2-propenoate.

Stage G: Methyl 3-[3-(4-chlorophenylsulfonyl)aminochroman-8-yl]propanoate

The compound obtained in the above stage is hydrogenated in acetic acid at 70° C. and at a pressure of 3 bar in the presence of palladium on charcoal. When 2 equivalents of hydrogen have been absorbed, perchloric acid is added at 70° C. and the hydrogenolysis is continued. The product is then treated under the same conditions as those described in Stage F of Example 10.

Stage H: 3-[3-(4-Chlorophenylsulfonyl)aminochroman-8-yl]propionic acid

The expected product is obtained by saponification of the compound described in the above stage under the conditions described in Stage K of Example 10.

Elemental microanalysis:

|  | C % | H % | N % | S % |
| --- | --- | --- | --- | --- |
| calculated | 54.61 | 4.58 | 3.54 | 8.10 |
| found | 54.51 | 4.50 | 3.68 | 7.90 |

EXAMPLE 17

3-[3-(4-Fluorophenylsulfonyl)aminochroman-8-yl]propionic acid

The expected product is obtained according to the process described in Example 16, using 4-fluorophenylsulfonyl chloride.

Elemental microanalysis:

|  | C % | H % | N % | S % |
| --- | --- | --- | --- | --- |
| calculated | 56.98 | 4.78 | 3.69 | 8.45 |
| found | 56.46 | 5.03 | 3.60 | 8.55 |

PHARMACOLOGICAL STUDY OF THE DERIVATIVES OF THE INVENTION

EXAMPLE 18: Platelet aggregation in rabbits

Rabbits (2–3 kg) are anesthetized with pentobarbital sodium (30 mg/kg i.v.). After cannulation of the left carotid artery, blood is withdrawn onto sodium citrate (0.109M) (1 vol. of citrate per 9 vol. of blood).

Platelet-rich plasma (PRP) is obtained by centrifugation (20° C.) at 250 g for 20 minutes, and platelet-poor plasma (PPP) by centrifugation at 1000 g (10 min). The number of platelets (PL) in the PRP is adjusted to between 300–350,000 PL/mm$^3$ by dilution with autologous PPP. The PRP is stored at the temperature of the room until the time of the test, and is used within 4 hours following withdrawal.

Platelet aggregation is carried out at 37° C. in siliconed glass tubes using an aggregometer. The PRP and PLs are stirred at 1000 rpm (revolutions per minute). In order to study the activity of thromboxane antagonists, the PRP is incubated for 1 min at 37° C., and the antagonist is then added for a period of 3 min before addition of the agonist U46619 (1 mM). The final volume in the cell is then 250 ml. The intensity of platelet aggregation is established by taking the maximum amplitude of the aggregation plots and is expressed as a percentage light transmission (% T). The activity of the antagonists is expressed as $IC_{50}$, that is to say the concentration of the substance which induces a 50% inhibition of the aggregation response induced by U46619.

The compounds of the invention inhibit platelet aggregation induced by the $TXA_2$ agonist, U46619. The $IC_{50}$s illustrated in the table below show that the compounds of the invention have an activity equal to or greater than that of the reference compound, BAY U3405.

| Example | $IC_{50}$ (µM) Rabbit |
| --- | --- |
| ex. 1 | 0.24 |
| ex. 2 | 0.82 |
| ex. 3 | 0.27 |
| ex. 4 | 0.16 |
| ex. 6 | 0.060 |
| ex. 9 | 0.32 |
| ex. 10 | 0.18 |
| ex. 11 | 0.67 |
| ex. 12 | 0.097 |
| ex. 13 | 0.16 |
| ex. 16 | 0.25 |
| ex. 17 | 1.1 |
| BAY U3405 | 1.10 |

EXAMPLE 19: Platelet aggregation in dogs

After anesthetizing the animal with pentobarbital sodium (30 mg/kg i.v.), arterial blood is withdrawn onto sodium citrate (0.109M) (1 vol. of citrate per 9 vol. of blood). The platelet-rich plasma (PRP) is obtained after centrifugation (20° C.) at 200 g for 10 minutes. The number of platelets in the PRP is, on average, 300,000 PL/mm$^3$ The PRP is stored at the temperature of the room until the time of the test, and is used within 4 hours following withdrawal.

Dog platelets respond weakly to U46619 alone. The addition of adrenalin, which by itself does not induce aggregation, makes it possible to obtain a more pronounced aggregation response to U46619. The PRP is incubated at 37° C. in the presence of the antagonist to be tested for 3 minutes. Aggregation is subsequently obtained by the addition of adrenalin (10µM) followed by that of U46619 (1 mM) 30 seconds later. The effect of the antagonists is measured and the $IC_{50}$ is determined as the antagonist concentration necessary to produce 50% inhibition of the aggregation responses to U46619 +adrenalin.

The compounds of the invention inhibit platelet aggregation induced by the TXA$_2$ agonist, U46619. The IC$_{50}$s illustrated in the table below show that the compounds of the invention have an activity equal to greater than that of the reference compound, BAY U3405.

| Example | IC$_{50}$ (µM) Dog |
| --- | --- |
| ex. 1 | 0.028 |
| ex. 2 | 0.083 |
| ex. 3 | 0.010 |
| ex. 4 | 0.010 |
| ex. 6 | 0.003 |
| ex. 8 | 0.15 |
| ex. 9 | 0.015 |
| ex. 10 | 0.011 |
| ex. 11 | 0.056 |
| ex. 12 | 0.012 |
| ex. 13 | 0.042 |
| ex. 16 | 0.020 |
| BAY U3405 | 0.110 |

EXAMPLE 20: Platelet aggregation in man

Venous blood is obtained from human volunteers who have taken no aspirin for at least 14 days preceding the experiment. Blood is withdrawn onto sodium citrate (0.109M) (1 vol. of citrate per 9 vol. of blood). Platelet-rich plasma (PRP) is obtained after centrifugation (20° C.) at 200 g for 10 minutes. The number of platelets is, on average, 250,000 PL/mm$^3$. The PRP is stored at the temperature of the room until the time of the test, and is used within 2 hours following withdrawal. The antagonists are tested according to the procedure described in Example 19, using U46619 at the concentration of 0.3 mM.

The compounds of the invention inhibit platelet aggregation induced by the TXA$_2$ agonist, U46619. The IC$_{50}$ of the compound of Example 1 is 84 nM, whereas that of the reference product BAY U3405 is 180 nM.

EXAMPLE 21: Specific binding to human platelet membranes

The tests of specific binding to platelet TXA$_2$ receptors are performed using $^3$H-SQ29548 as ligand (according to the protocol described by A. Hedberg et al., J. Pharm. Exp. Ther., 245, 786–792, 1988). The experiments take place at a temperature of 25° C. in a final reaction volume of 0.2 ml in the presence of 0.1 mg of platelet membranes, prepared from washed, ground and centrifuged human platelets. Determination of the activity of the products of the invention is made by competition experiments, in which increasing concentrations of product are placed in the presence of a fixed concentration of $^3$H-SQ29548. This protocol makes it possible to produce inhibition curves for each antagonist studied. The 50% inhibitory concentration is determined by non-linear regression by the "Simplex" method described by M. S. Caceci et al., (Byte, 340–362, May 1984) calculated according to the mass action law model of C. Michaelis et al. (Biochem. Zeitschrift, 49, 333–369, 1913). The inhibition constant is then determined using the formula of Cheng and Prusoff (Biochem. Pharmacol., 22, 3099–3108, 1973). The substances of the invention inhibit the specific binding of $^3$H-SQ29548. The Ki of the compound of Example 1 is 0.96 nM, which demonstrates a strong affinity for the platelet TXA$_2$ receptors. This activity is higher than that of the reference, BAY U3405, which gives a Ki of 3.61 nM in this same test.

EXAMPLE 22: ex vivo platelet aggregation in dogs

The experiments are carried out on non-anesthetized dogs. After applying a tourniquet and introduction of a needle into the cephalic vein, blood is withdrawn onto sodium citrate (0.109M). The blood is stored at the temperature of the room. Platelet aggregation is measured in the total blood using an impedance probe in an aggregometer. The pro-aggregating activity of the thromboxane receptor agonist, U46619, is tested in the presence of adrenalin (10 µM). The products of the invention and the reference substances are administered to dogs orally after performing the control test. Blood samples are subsequently withdrawn at determined times: t=30 min, 1 h, 2 h, 4 h, 6 h, 24 h, 48 h, etc. until the aggregation activity of U46619 has fully returned. The products of the invention completely inhibit ex vivo platelet aggregation induced by U46619. The compound of Example 1 at doses of 10 to 3000 µg/kg completely inhibits the platelet aggregation of U46619 for at least 3 days, and up to 11 days for the highest dose. Afterwards, the pro-aggregating activity of U46619 gradually returns. The compound of Example 1 at the dose of 10 µg/kg per os completely inhibits the platelet aggregation of U46619 for at least 3 days. At the highest dose of 100 µg/kg per os, it inhibits the platelet aggregation of U46619 for at least 8 days. The same result was obtained with 3 mg/kg per os of this compound. The compound of Example 10 at the dose of 100 µg/kg per os inhibits platelet aggregation induced by U46619 for 5 days. The anti-aggregating effect of the compounds of the invention is longer lasting than that observed with BAY U3405. Indeed, at the dose of 100 µg/kg per os, the total inhibition of aggregation obtained with BAY U3405 lasts only 6 hours. The experiments show that the compounds of the invention are well-absorbed orally and have a very considerable duration of action on platelet TXA$_2$ receptors.

EXAMPLE 23: Experimental thrombosis in guinea pig carotid artery

The technique recently described by Roux et al., Thrombosis and Haemostasis, 71, 252–256 (1994), was used in order to measure the anti-thrombotic effect of our products. Male guinea pigs (390 to 420 g) were anesthetized with ketamine hydrochloride (90 mg/kg i.m.) and xylazine (12 mg/kg i.m.). A catheter is introduced into the left jugular vein in order to allow the i.v. injection of the substances. The right carotid artery is prepared and a Doppler probe (20 MHz) is installed, which allows the blood flow to be measured. At a distance of two mm from the Doppler probe a subendothelial lesion is produced using a clamp ("pinching"). After introduction of this lesion, the blood flow decreases and stops altogether (between 1 and 2 min). When the flow is at zero, the artery is touched, which removes the occlusive thrombus and restores the flow (see Roux et al., 1994). This thrombotic process is repeated and the cyclic decreases in the flow (CFV=cyclic flow variations) are expressed as a number per 20 min. In control carotid arteries (n=4), the CFVs are counted over 2 periods of 20 min: during the first period, 9±1 CFV/20 min are counted; during the second period, 8±1 CFV/20 min are counted. In a group of animals (n=3) treated with the compound of Example 1, 10±2 CFV/20 min are counted before the treatment and 0.3±0.3 CFV/20 min are counted alter an i.v. injection of 100 µg/kg. These results demonstrate a powerful anti-thrombotic effect.

EXAMPLE 24: Pharmaceutical composition

Formula for the preparation of 1000 tablets containing a 10 mg dose

| Compound of Example 1 | 10 g |
|---|---|
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

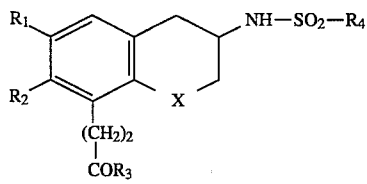

in which:

$R_1$ and $R_2$, which may be identical or different, represent hydrogen, but not simultaneously when X=CH$_2$, halogen, linear or branched ($C_1$–$C_6$) alkyl, phenyl which is unsubstituted or substituted with one or more halogen or linear or branched ($C_1$–$C_6$) alkyl or linear or branched ($C_1$–$C_6$) alkoxy or trihalomethyl or benzyl, pyridylmethyl or imidazolylmethyl, thiazolylmethyl, pyridyl, imidazolyl, or thiazolyl, or alternatively, $R_1$ and $R_2$ form, with the carbon atoms to which they are attached, a cyclopentane or cyclohexane ring, $R_3$ represents hydroxyl, linear or branched ($C_1$–$C_6$) alkoxy or amino which is unsubstituted or substituted with one or two linear or branched ($C_1$–$C_6$) alkyl, $R_4$ represents linear or branched ($C_1$–$C_6$) alkyl, phenyl which is unsubstituted or substituted with one or more halogen or linear or branched ($C_1$–$C_6$) alkyl, linear or branched ($C_1$–$C_6$) alkoxy, trihalomethyl or hydroxyl, naphthyl, pyridyl, thienyl, or thiazolyl, X represents methylene or oxygen or sulfur, their enantiomers or their addition salts with a pharmaceutically-acceptable base.

2. A compound of claim 1 in which $R_1$ represents hydrogen or methyl.

3. A compound of claim 1 in which $R_2$ represents methyl.

4. A compound of claim 1 in which X represents methylene.

5. A compound of claim 1 which is 3-{6-[(4-chlorophenylsulfonyl)amino]-2-methyl-5,6,7,8-tetrahydronaphth-1-yl}propionic acid, or an addition salt with a pharmaceutically-acceptable base.

6. A method for treating a mammal afflicted with a condition requiring an antithrombotic comprising the step of administering to the mammal an amount of a compound of claim 1 which is effective for alleviation of said condition.

7. A pharmaceutical composition useful as an antithrombotic comprising as active principle an effective antithrombotic amount of a compound as claimed in claim 1, together with a pharmaceutically-acceptable excipient or vehicle.

* * * * *

UNITED STATES PATENT AND TRADEMARK OFFICE
CERTIFICATE OF CORRECTION

PATENT NO. : 5,472,979
DATED : Dec. 5, 1995      Page 1 of 6
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Title Page, [57] ABSTRACT, line 1: Add -- A compound of formula (I): -- (before the formula). Pg. 1 of Abstract, line 1

Column 4, line 46: "R2" should read -- $R_2$ --.

Column 5, line 29 (approx.): "R2" should read -- $R_2$ --.

Column 5, line 44: "R2, R3" should read -- $R_2$, $R_3$ --.

Column 5, line 55: "a" should read -- a: --. Pg. 6, line 15

Column 11, line 15: Add -- ]- -- to end of the line.

Column 11, line 16: Delete "]-" from the beginning of the line.

Column 12, line 38: "22 mmol ...." should start a new paragraph.

UNITED STATES PATENT AND TRADEMARK OFFICE
CERTIFICATE OF CORRECTION

PATENT NO. : 5,472,979
DATED : Dec. 5, 1995
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Column 13, line 2: "4 mmol of the ....." should start a new paragraph.

Column 13, line 47: Delete the dash and add -- 1)- -- to the end of the line.

Column 13, line 48: Delete "1)" from the beginning of the line

Column 14, line 12: Delete spaces before and after " } ".

Column 15, line 63: "14.7 mmol of the compound....." should start a new paragraph.

Column 16, line 41 (approx.): Add -- ]- -- to end of the line.

Column 16, line 42 (approx.): Delete "]-" from the beginning of the line.

Column 18, line 28: "To 11.8 mmol of ...." should start a new paragraph.

UNITED STATES PATENT AND TRADEMARK OFFICE
CERTIFICATE OF CORRECTION

PATENT NO. : 5,472,979
DATED : Dec. 5, 1995
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Column 19, line 12: Add -- ]- -- to end of the line.

Column 19, line 13: Delete "]-" from beginning of the line.

Column 20, line 44: Add -- ]- -- to end of the line.

Column 20, line 45: Delete "]-" from beginning of the line.

Column 20, line 62: Add -- ]- -- to end of the line.

Column 20, line 63: Delete "]-" from the beginning of the line and Add -- } -- to the end of the line.

Column 20, line 64: Delete "}" from the beginning of the line.

Column 21, line 7: "To 1 g of ...." should start a new paragraph.

Column 21, line 10: Add a -- ) -- to the end of the line ahead of the dash.

UNITED STATES PATENT AND TRADEMARK OFFICE
CERTIFICATE OF CORRECTION

PATENT NO. : 5,472,979
DATED : Dec. 5, 1995           Page 4 of 6
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Column 21, line 11: Delete ")" from the beginning of the line.

Column 21, line 50: Add -- ]- -- to end of the line.

Column 21, line 51: Delete "]-" from the beginning of the line.

Column 21, line 66: Delete the dash and add -- 1)--- to the end of the line.

Column 21, line 67: Delete "1)" from the beginning of the line.

Column 22, line 15: Delete the dash and add -- )- -- to the end of the line.

Column 22, line 16: Delete ")" from the beginning of the line.

Column 22, line 35: "To 800 mg ....." should start a new paragraph.

Column 22, line 53: Add -- ]- -- to the end of the line.

UNITED STATES PATENT AND TRADEMARK OFFICE
CERTIFICATE OF CORRECTION

PATENT NO. : 5,472,979
DATED : Dec. 5, 1995
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Column 22, line 54: Delete "]-" from the beginning of the line.

Column 22, line 55: "naphth-1yl}" should read -- naphth-1-yl} --.

Column 23, line 13: "Stage c:" should read -- Stage C: --.

Column 23, line 47: Add -- yl] -- to the end of the line. Pg. 32, line 1

Column 23, line 48: Delete "yl]" from the beginning of the line.

Column 27, line 33: After "trihalomethyl" change the "or" to a comma.

UNITED STATES PATENT AND TRADEMARK OFFICE
CERTIFICATE OF CORRECTION

PATENT NO. : 5,472,979
DATED : Dec. 5, 1995
INVENTOR(S) : Gilbert Lavielle, Thierry Dubuffet, Olivier Muller, Michel Laubie, Tony Verbeuren, Serge Simonet, Jean-Jacques Descombes It is certified that error appears in the above-indentified patent and that said Letters Patent is hereby corrected as shown below:

Column 27, line 34: Change "or" to a comma.

<u>Claim 1, line 7</u>.

Column 28, line 14: Add a -- , -- (comma) after "enantiomers".

Column 28, line 23: Add -- thereof -- after "salt".

Signed and Sealed this

Sixteenth Day of April, 1996

Attest:

BRUCE LEHMAN

Attesting Officer

Commissioner of Patents and Trademarks